(12) United States Patent
Johnson

(10) Patent No.: US 6,893,632 B2
(45) Date of Patent: May 17, 2005

(54) ODOR ELIMINATION METHODS USING ZEOLITE-CONTAINING LIQUID SPRAYS AND DETERGENT

(76) Inventor: Louis B. Johnson, 401 Love St., Troy, AL (US) 36081

(\*) Notice: Subject to any disclaimer, the term of this patent is extended or adjusted under 35 U.S.C. 154(b) by 0 days.

(21) Appl. No.: 10/141,075

(22) Filed: May 9, 2002

(65) Prior Publication Data

US 2002/0146383 A1 Oct. 10, 2002

Related U.S. Application Data

(63) Continuation-in-part of application No. 09/574,208, filed on May 19, 2000, now Pat. No. 6,440,415.
(60) Provisional application No. 60/136,760, filed on May 28, 1999.

(51) Int. Cl.[7] .............................................. A01N 25/08
(52) U.S. Cl. ...................... 424/76.1; 424/400; 424/401; 424/402; 424/404; 424/682; 424/683; 424/684; 428/402; 510/532
(58) Field of Search ................................ 424/400, 402, 424/403, 405, 682, 684, 76.1, 76.21, 76.9, 489, 76.3, 65, 404; 428/402; 510/532

(56) References Cited

U.S. PATENT DOCUMENTS

| | | | |
|---|---|---|---|
| 3,586,596 A | \* | 6/1971 | Ainsworth et al. |
| 4,078,050 A | | 3/1978 | Hart |
| 4,181,712 A | \* | 1/1980 | Rialdi |
| 4,795,482 A | | 1/1989 | Gioffre et al. |
| 4,833,181 A | \* | 5/1989 | Narukawa et al. |
| 5,190,663 A | | 3/1993 | Fetzer |
| 5,197,208 A | \* | 3/1993 | Lapidus |
| 5,258,414 A | | 11/1993 | Bergishagen |
| 5,383,236 A | \* | 1/1995 | Sesselmann |
| 5,429,628 A | | 7/1995 | Trinh et al. |
| 5,539,930 A | \* | 7/1996 | Sesselmann |
| 5,585,107 A | | 12/1996 | Vickers |
| 5,593,670 A | | 1/1997 | Trinh et al. |
| 5,780,020 A | \* | 7/1998 | Peterson et al. |
| 5,790,987 A | \* | 8/1998 | Sesselmann |
| 5,861,144 A | \* | 1/1999 | Peterson et al. |
| 5,874,067 A | \* | 2/1999 | Lucas et al. |
| 5,882,638 A | \* | 3/1999 | Dodd et al. |
| 5,885,599 A | | 3/1999 | Peterson et al. |
| 5,891,391 A | | 4/1999 | Fore |
| 6,039,892 A | | 3/2000 | Himeshima et al. |
| 6,100,233 A | | 8/2000 | Sivik et al. |
| 6,218,013 B1 | | 4/2001 | Wood et al. |
| 6,350,459 B1 | | 2/2002 | Suzuki et al. |

FOREIGN PATENT DOCUMENTS

| | | | |
|---|---|---|---|
| EP | 0392528 | \* | 10/1990 |
| GB | 2169276 | \* | 7/1986 |
| JP | 55132619 | \* | 10/1980 |
| WO | 9817239 | \* | 4/1998 |

OTHER PUBLICATIONS

"Disappearing Act!", Buckmasters Whitetail Magazine, Sep. 1991.\*
"The Hunter's Edge Story", Edge Outfitters, Sep. 1991.\*
"Cloth, Laminated, Nylon Tricot Knit, Polyurethane Foam, Laminate, Chemical Protective, and Flame Resistant", Military Specification, Jan. 1986.\*
advertisement, North American Whitetail Magazine, Sep. 1988.

\* cited by examiner

*Primary Examiner*—Neil S. Levy
(74) *Attorney, Agent, or Firm*—Clark & Brody

(57) ABSTRACT

A regimen for hunting includes using a number of zeolite-containing personal items in connection with a hunter's apparel and body to reduce the hunter's scent for improved hunting. The personal items include mouthwash, deodorant/anti-perspirant, body and boot powder, bar and liquid soap for cleansing the body and hair, laundry detergent and dryer sheets. Each of the personal items includes an effective amount of zeolite, so that use of the personal items reduces the available scent to be detected by animals in the wild. The regimen can also include the use of a seat cushion that is covered with an activated carbon-containing fabric for odor control and/or elimination.

8 Claims, 1 Drawing Sheet

ODOR ELIMINATION METHODS USING ZEOLITE-CONTAINING LIQUID SPRAYS AND DETERGENT

This is a continuation-in-part application based on application Ser. No. 09/574,208, filed on May 19, 2000, now U.S. Pat. No. 6,440,415, which is based on provisional application Ser. No. 60/136,760 filed on May 28, 1999.

FIELD OF THE INVENTION

The present invention is directed to odor eliminating items and methods of use, and in particular to personal items using zeolites for use prior to or during hunting.

BACKGROUND ART

In the prior art, the use of activated carbon or charcoal on hunting clothes or other hunting-related apparel for masking the scent of a hunter is known. U.S. Pat. No. 5,539,930 to Sesselmann discloses such an application. This patent incorporates activated charcoal as part of a hunter's clothing to absorb human odors and prevent such odors from signaling wild game of the presence of humans.

Activated charcoal and zeolites are also used in compositions for controlling malodors on human skin as described in U.S. Pat. No. 5,874,067 to Lucas et al. In this patent, the composition may optionally contain hydrophobic antimicrobials, zinc salts, activated carbon, etc. U.S. Pat. No. 5,861,144 to Peterson et al. discloses a moisture and odor absorbing powder composition, which may contain additional odor controlling agents such as zeolites, activated charcoal, sodium bicarbonate, antimicrobial agents, and antiperspirants. Both of these patents are primarily directed to the use of cyclodextrins for odor control, and are not concerned with odor elimination in the field of hunting. In fact, cyclodextrin has a number of attributes that make it undesirable for hunting, e.g., stickiness, attraction to hydrocarbons, including perfumes, and the like, and its use would not be contemplated in a hunting product that is intended to be odor free.

Spray products containing activated carbon for use in hunting are known. Robinson Laboratories of Cannon Falls of Minnesota manufactures such a product. A similar product was made by Johnson Laboratories of Troy, Ala. Typically, these spray products may contain other known scent eliminators in the spray as well as the activated carbon. The Johnson product is described in patent application Ser. No. 09/574,208 filed on May 19, 2000, and this patent application is herein incorporated by reference in its entirety.

Activated carbon spray products, while being effective for odor elimination, are disadvantageous due to their smutting characteristic. Because of the dark or black nature of the carbon, whether as carbon or charcoal, applying the powder in a spray to a particular surface can give the surface a dark hue, which may also be unpleasant depending on the type of surface. For instance, when applied to hunter's clothes that have a camouflage pattern, the smutting is not objectionable since the dark hue is masked by the camouflage pattern. In other instances, the smutting presents an undesirable look, and improvements are still needed in this area. In fact, However, a need still exists to further mask human odors during hunting. In response to this need, the present invention utilizes effective amounts of activated carbon to eliminate odors, particularly odors from humans as part of a hunting regimen.

Another problem facing hunters is the generation of odors via perspiration and the like caused by extended periods of sitting in a tree stand or other hunting structure. While there are many types of cushions available for this purpose, none are specifically designed for odor elimination and comfort. The invention solves this problem by combining such a cushion with a fabric that contains activated carbon for odor elimination. The fabric is situated at least on a face of the seat, which receives the hunter's body so that perspiration or other odors emanating from the hunter can be adsorbed by the activated carbon in the fabric.

Activated carbon containing fabric for hunting apparel and other items is known, see U.S. Pat. Nos. 5,383,236 5,539,930, 5,790,987, and 6,009,559 to Sesselmann, and these patents are herein incorporated by reference in their entirety. However, these patents do not teach the use of such a fabric on a seat cushion that supports a hunter.

SUMMARY OF THE INVENTION

It is a first object of the present invention to provide improved ways to mask human odors, especially for hunting.

A further object of the invention is an odor eliminating spray having a zeolite as a component thereof.

Yet another object of the invention is a soap, either a liquid hair and body soap or a bar soap containing effective amounts of a zeolite.

One other object of the invention is a laundry detergent, either liquid or powder, containing zeolite in amounts effective to remove odors during washing.

Still other objects of the invention are a boot or body powder, a stick deodorant-antiperspirant, a mouthwash, or a dryer sheet or other fabric, each containing effective amounts of the zeolite for odor control.

One other object of the invention is the use of the items listed above in conjunction with hunting apparel or a hunter, either alone or in combination. Certain items may be used prior to or during hunting.

A still further object of the invention is a cushion that uses an activated carbon containing fabric for odor elimination and control when a hunter is sitting on the cushion as well as use of such a cushion for hunting.

Other objects and advantages of the present invention will become apparent as a description thereof proceeds.

In satisfaction of the foregoing objects and advantages, the present invention provides a regimen of treatment in preparation for hunting or during hunting. The regimen includes the use of one or more personal items as each relates to the hunter, and the use of a number of other items for treating hunting apparel.

In one mode, the invention entails a method of preparing for hunting by applying a powder containing an amount of zeolite up to 5.0% by weight to hunting apparel to be worn for hunting. The regimen also includes washing hunting apparel in a powdered laundry detergent containing an amount of zeolite up to 5.0% by weight or a liquid laundry detergent containing an amount of zeolite up to 10.0% by weight. As part of the washing step, dryer sheets could be used during machine drying, wherein the dryer sheet contains an amount of zeolite up to 5.0% by weight. A liquid spray could be applied to the hunting apparel, the spray containing an amount of zeolite up to 5.0% by weight to the hunting apparel to be worn for hunting or being worn for hunting. One, two or all of the steps described above can be performed in preparation for hunting. Application of the spray or powder could also be done during hunting as needed.

In another mode, the method of preparing for hunting includes applying a liquid spray or a powder, each containing an amount of zeolite up to 5.0% by weight, to at least a portion of a hunter's body prior to or during hunting. All or a portion of the hunter's body can be washed with one of a liquid or a bar soap, the liquid soap containing an amount of zeolite up to 3.0% by weight, and the bar soap containing an amount of zeolite up to 5.0% by weight. The hunter can use a mouthwash containing an amount of zeolite up to 1.0% by weight, and apply a deodorant or anti-perspirant containing an amount of zeolite up to 1.0% by weight. Any one or all of the steps relating to personal hygiene can be used. In addition, the personal hygiene steps can be combined with one or more of the steps for treating the hunting apparel.

Preferably, for the personal hygiene items, the zeolite amount ranges between 0.1 and 2.0% by weight for the liquid soap, between 0.1 and 4.0% by weight for the bar soap and the body powder, and between 0.1 and 0.5% by weight for deodorant or antiperspirant, and mouthwash.

When treating the apparel, the zeolite preferably ranges between 0.1 and 4.0% for the liquid spray, the liquid laundry detergent, the dryer sheet, and the powder, and between 0.1 and 5.0% for the powdered laundry detergent.

The invention also includes the items to be used for treating the apparel, namely, the powdered and liquid laundry detergent, the dryer sheets, a powder such as a boot powder, and liquid spray. The invention also encompasses the personal hygiene items of the body powder, the liquid and bar soaps, the mouthwash, and the deodorant/antiperspirant. These items have the zeolite contents as shown above.

The invention also includes an improved cushion for hunting purposes. The cushion is used for seating comfort when the hunters are sitting or resting during the actual hunt. At least the portion adapted to contact the hunter is covered with a fabric containing activated carbon for odor elimination. The fabric can cover the entire cushion and be removable as well.

BRIEF DESCRIPTION OF THE DRAWINGS

Reference is now made to the drawings of the invention wherein.

DESCRIPTION OF THE PREFERRED EMBODIMENTS

Figure 1:
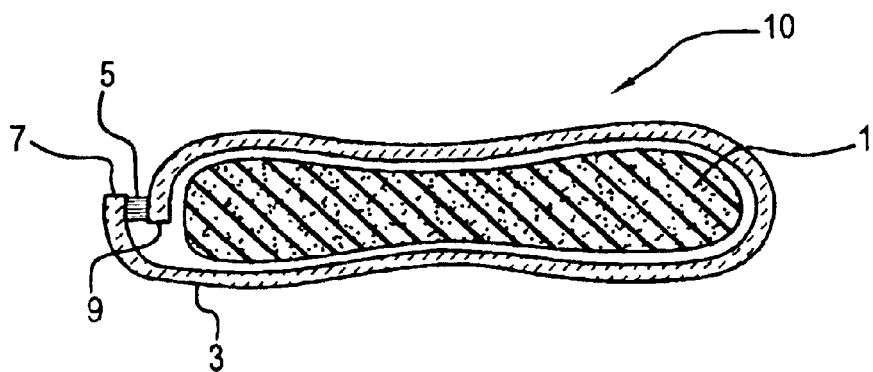
FIG. 1 is a cross sectional view of cushion embodiment of the invention.

In one aspect of the invention, a regime of preparation is employed whereby a number of steps can be taken in preparation of hunting that will reduce or mask the odor or scent of a person intending to go hunting.

In a first aspect, one's clothes or skin could be sprayed with a liquid spray composition containing zeolite for odor control. The base of the spray can be water with sodium carbonate or bicarbonate and/or potassium carbonate or bicarbonate. The zeolite in the spray can range up to 5.0% by weight, more preferably between 0.1 and 4.0%. Other scent eliminators used in hunting can also be included. One example is that disclosed in U.S. Pat. No. 4,078,050 to Hart, which is herein incorporated by reference in its entirety.

A second aspect would be to wash one's clothes using a liquid or powder detergent containing zeolite. When using a liquid detergent, the base could be a conventional surfactant blend such as coconut oil amide. The zeolite in weight percent can range up to 5.0% by weight, preferably between 0.1 and 4.0%. The powdered laundry detergent can have a soda ash and sodium sulfate base, and can contain up to 10.0% by weight zeolite, preferably between 0.1 and 5.0%.

A third aspect of the regimen would be for a hunter to use a mouthwash and/or a stick deodorant/antiperspirant prior to hunting. The mouthwash could employ water as a base and the zeolite could range up to 1.0% by weight, preferably between 0.1 and 0.5%. The deodorant-antiperspirant can have a typical glycol base, and the amount of zeolite can range up to 1.0% by weight, preferably between 0.1 and 0.5%.

A fourth aspect would be to dust the hunter's footwear, e.g., boots, and body with a powder. The powder can be a talc, sodium bicarbonate, and corn starch combination, and the weight percentage of zeolite can be up to 5.0%, preferably between 0.1 and 4.0%.

A fifth aspect involves washing the hunter's skin with bar soap, washing the hunter's hair with a liquid soap, and using dryer sheets when drying the hunter's clothes. The bar soap can be a typical tropical oil base soap, and have a weight percentage of zeolite of up to 5.0%, preferably between 0.1 and 4.0%. The liquid soap can be either an ammonium or sodium laurel sulfate or a coconut oil amide. The zeolite weight percentage can be up to 3.0%, preferably between 0.1 and 2.0%. The dryer sheets can be impregnated with up to 5.0% by weight zeolite, preferably between 0.1 and 4.0%.

One or a combination of the above steps can be employed as a precursor to actual hunting, or during hunting. By using zeolite in connection with the personal items such as soaps, mouthwashes, detergents, etc., less scent is available to alert animals that hunters are nearby. With less warning to the animals, more success in hunting can be achieved. The use of zeolite also overcomes the smutting problem that exists when activated carbon is sprayed on hunter's apparel.

Zeolite in the context of this invention is intended to encompass natural zeolites, synthetic zeolites, and modified zeolites. Preferred zeolites are modified ones such as Union Carbide's HiSiv™ or one as disclosed in U.S. Pat. No. 4,795,482 to Gioffre et al. that is herein incorporated in its entirety by reference. While many zeolites or molecular sieves are naturally hydrophilic, this type is also hydrophobic and organophilic. As such, they are highly efficient at adsorbing unwanted compounds, even at relatively high humidity. Since hunting environments can often be humid, zeolites of this nature offer superior odor elimination over activated carbon. A further description of these types of zeolites is not necessary. It should also be understood that the inventive composition and use do not use cyclodextrin since it is detrimental to the odor elimination needs of a hunter.

It should also be understood that the zeolite could be employed in the stated amounts in other known compositions for the various items disclosed herein. The import of the invention lies in the use of zeolite, particularly in the various items associated with the hunter and the hunter's apparel as a cumulative regimen to reduce human odors or scents. Soaps, powders, mouthwashes, deodorants/antiperspirants, dryer sheets or other fabrics, detergents (liquid or powdered), and sprays having bases other than those disclosed above could also be modified with the effective amounts of zeolite for scent reduction.

The invention also entails a hunting item in the form of a cushion used for seating in a tree stand, hunting shack, blind, or other hunting structure. Often time, hunters will have to sit for extended periods of time, and this sitting can generate sweat and unwanted body odors. The cushion is covered with a fabric that uses activated carbon for odor control. A preferred fabric is that sold under the name Scent-Lok®, and generally described in the Sesselmann patents noted above, and it is readily available in stores and other places of business. In general, this type of a fabric has a laminate or single layer structure wherein at least one layer incorporates activated carbon or charcoal. Many different fabric constructions have been employed for this purpose and the Scent-Lok® fabric is one example of that which can be used in combination with the cushion.

The cushion design can be any type that provides resiliency for the hunter. Many different types of cushions are available for hunting purposes, and any of these types can be used in the invention. The fabric can be made to cover the entire layer, and it can include a zipper, snaps, hook and loop means, or other type opening for easy removal and installation. Making the cover removable permits the fabric to be removed for regeneration of the activated carbon. In another mode, the fabric could cover just the surface of the cushion adapted to contact a portion of the hunter's body, and the fabric could be attached to the cushion using fasteners such as snaps, bands, hook and loop fasteners, and the like. This mode requires the fabric to attach to the cushion, whereas in the other mode, the fabric covers the cushion, and has entry means for cushion insertion into the cavity formed by the fabric. In either mode, the mode of attaching the fabric to the cushion allows the fabric to be easily removed for replacement or regeneration of the activated carbon.

Figure 2:
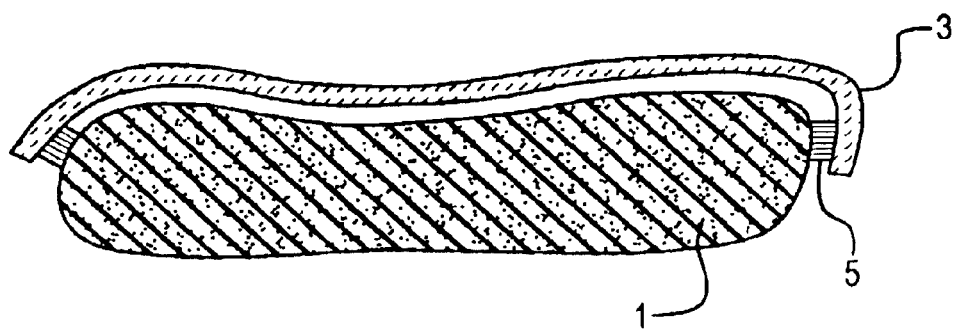
FIG. 2 is cross sectional view of a second cushion embodiment of the invention.

FIG. 1 shows a cross section of an exemplary cushion assembly 10. The cushion 1 can be square, rectangular, oval or any shape. In the FIG. 1 embodiment, the cushion 1 is shown surrounded by the fabric 3. A hook and loop fastener 5 is depicted to connect the ends 7 and 9 of the fabric. The fabric is shown as a single layer but is intended to represent a single layer or laminate structures that employ activated carbon. FIG. 2 shows the cushion 10 with the fabric 11 covering just a top portion thereof. Hook and loop fasteners 5 are employed to keep the peripheral edge 13 of the fabric secured to the cushion 1.

It is also believed that using the fabric over the cushion offers better odor control than incorporating the carbon into the cushion itself. This would significantly increase the cost of the cushion, and make it difficult to regenerate the carbon as is done with the fabric. Further, use of the fabric presents a concentrated zone of activated carbon adjacent the hunter's body, and such would not be achieved where the activated carbon was dispersed throughout the cushion, e.g., dispersed in the foam material used for the cushion. The fabric should be used as an exterior fabric of the cushion, such that the underlying cushion construction can vary as just a foam material, a foam material covered with a typical cushion-covering fabric material, and the like.

In use, a hunter would carry the cushion to the hunting site, and place it on a particular structure, e.g., a chair, bench, tree stand, ledge, or the like, and the hunter would either sit on the cushion or rest another body part thereon during the hunting period. When the hunt is over, the fabric, if removable, can be removed from the cushion by undoing the fasteners and washed for subsequent use. The fabric when worn out can be easily replaced with new fabric as well.

While the cushion or the method of using the cushion is primarily designed for sitting so as to contact a rear of a hunter, the cushion could also be configured to contact other body parts that would normally rest on a hunting structure such as a bench, chair, ledge rail, or the like. Typical body parts would include elbows, backs, knees, legs, etc.

As such, an invention has been disclosed in terms of preferred embodiments thereof which fulfills each and every one of the objects of the present invention as set forth above and provides new and improved ways to control and/or eliminate human odors for hunting.

Of course, various changes, modifications and alterations from the teachings of the present invention may be contemplated by those skilled in the art without departing from the intended spirit and scope thereof. It is intended that the present invention only be limited by the terms of the appended claims.

What is claimed is:

1. A method of preparing for hunting comprising
   a) washing hunting apparel in a powdered laundry detergent containing an amount of zeolite up to 5.0% by weight or a liquid laundry detergent containing an amount of zeolite up to 10.0% by weight; and
   b) applying a liquid spray containing an amount of zeolite up to 5.0% by weight to the hunting apparel to be worn for hunting.

2. The method of claim 1, wherein the zeolite ranges between 0.1 and 4.0% for the liquid spray and between 0.1 and 5.0% for the powdered laundry detergent.

3. The method of claim 1, wherein the zeolite is a modified zeolite that is organophilic and hydrophobic.

4. The method of claim 1, wherein the zeolite is one of a natural or synthetic zeolite.

5. A method of preparing for hunting comprising applying a liquid spray containing an amount of zeolite up to 5.0% by weight to the hunting apparel to be worn for hunting.

6. The method of claim 5, wherein the zeolite is a modified zeolite that is organophilic and hydrophobic.

7. The method of claim 5, wherein the zeolite ranges between 0.1 and 4.0%.

8. The method of claim 5, wherein the zeolite is one of a natural or synthetic zeolite.

* * * * *